United States Patent
Adachi et al.

(10) Patent No.: US 9,308,519 B2
(45) Date of Patent: Apr. 12, 2016

(54) ADSORBENT FOR ORGANIC FLUORO-COMPOUND COMPRISING CYCLODEXTRIN-SUPPORTED POLYMER

(71) Applicants: DAIKIN INDUSTRIES, LTD., Osaka-shi, Osaka (JP); OSAKA UNIVERSITY, Suita-shi, Osaka (JP)

(72) Inventors: Kenji Adachi, Settsu (JP); Masaki Kuramitsu, Settsu (JP); Mitsuru Akashi, Suita (JP); Toshiyuki Kida, Suita (JP)

(73) Assignees: DAIKIN INDUSTRIES, LTD., Osaka-Shi (JP); OSAKA UNIVERSITY, Suita-Shi (JP)

( * ) Notice: Subject to any disclaimer, the term of this patent is extended or adjusted under 35 U.S.C. 154(b) by 0 days.

(21) Appl. No.: 14/646,511

(22) PCT Filed: Nov. 19, 2013

(86) PCT No.: PCT/JP2013/081138
§ 371 (c)(1),
(2) Date: May 21, 2015

(87) PCT Pub. No.: WO2014/087838
PCT Pub. Date: Jun. 12, 2014

(65) Prior Publication Data
US 2015/0314266 A1 Nov. 5, 2015

(30) Foreign Application Priority Data
Dec. 7, 2012 (JP) ................................. 2012-268600

(51) Int. Cl.
| | | |
|---|---|---|
| *B01D 15/38* | (2006.01) | |
| *B01J 20/26* | (2006.01) | |
| *B01D 15/08* | (2006.01) | |
| *B01D 15/26* | (2006.01) | |
| *B01J 20/28* | (2006.01) | |
| *C07C 51/50* | (2006.01) | |
| *B01J 20/34* | (2006.01) | |
| *B01J 20/32* | (2006.01) | |
| *C02F 1/28* | (2006.01) | |
| *C08B 37/16* | (2006.01) | |
| *C08L 5/16* | (2006.01) | |
| *C02F 101/36* | (2006.01) | |

(52) U.S. Cl.
CPC ............... *B01J 20/265* (2013.01); *B01D 15/08* (2013.01); *B01D 15/265* (2013.01); *B01J 20/261* (2013.01); *B01J 20/28016* (2013.01); *B01J 20/321* (2013.01); *B01J 20/3274* (2013.01); *B01J 20/3425* (2013.01); *B01J 20/3475* (2013.01); *C02F 1/285* (2013.01); *C02F 1/288* (2013.01); *C07C 51/50* (2013.01); *C08B 37/0012* (2013.01); *C08B 37/0015* (2013.01); *C08L 5/16* (2013.01); *C02F 2101/36* (2013.01); *C02F 2303/16* (2013.01)

(58) Field of Classification Search
CPC ............... B01D 15/38; B01D 15/3804; B01D 15/3828; C02F 1/288
See application file for complete search history.

(56) References Cited

U.S. PATENT DOCUMENTS 4,169,079 A * 9/1979 Tabushi ............... C08B 37/0012
502/402
4,539,399 A * 9/1985 Armstrong ......... B01D 15/3833
210/502.1

FOREIGN PATENT DOCUMENTS

| JP | 59-228936 A | 12/1984 |
|---|---|---|
| JP | 2003-226755 A | 8/2003 |
| JP | 2012-101159 A * | 5/2012 |

OTHER PUBLICATIONS del Valle, Process Biochemistry, Cyclodextrins and their uses: a review, 2004, 39, pp. 1033-1046.*
Zaragoza Dorwald, Side Reactions in Organic Synthesis, 2005, Wiley-VCH Verlag GmbH & Co. KGaA, Weinheim, Preface. p. IX.*
Matsuzawa et al, Tetrahedron Letters, Efficient enantiomeric resolution via introduction of a fluorous tag as a resolving reagent with beta-cyclodextrin columns: model study on fluorinated O-acetylmandelate and ibuprofen amide, 2003 44, pp. 6227-6230.*
Kawano et al, Chemical Letters, Efficient Removal and Recovery of Perfluorinated Compounds from Water by Surface-tethered beta-Cyclodextrins on Polystyrene Particles, 2013, 42, pp. 392-394.*
International Search Report issued in PCT/JP2013/081138, mailed on Jan. 21, 2014.
Written Opinion issued in PCT/JP2013/081138, mailed on Jan. 21, 2014.
Translation of Written Opinion issued in PCT/JP2013/081138, dated Jun. 9, 2015.

* cited by examiner

*Primary Examiner* — Paul A Zucker
(74) *Attorney, Agent, or Firm* — Birch, Stewart, Kolasch & Birch, LLP

(57) ABSTRACT

The present invention is to provide a material that is capable of selectively adsorbing organic fluoro-compounds such as perfluorooctane sulfonic acid, allows the adsorbed organic fluoro-compounds to be recovered, and is reusable as an adsorbent, specifically to provide a polymer in which cyclodextrin is supported on the surface of a water-insoluble polymer, and an adsorbent containing the same, and a method of use of the same as a selective adsorbent of, in particular, an organic fluoro-compound.

6 Claims, 6 Drawing Sheets

ADSORBENT FOR ORGANIC FLUORO-COMPOUND COMPRISING CYCLODEXTRIN-SUPPORTED POLYMER

TECHNICAL FIELD

The present invention relates to an insoluble polymer with cyclodextrin supported on the surface of the insoluble polymer (also referred to simply as "cyclodextrin-supported polymer") and to the use of the polymer as an absorbing material.

BACKGROUND ART

Organic fluoro-surfactants such as perfluorooctane sulfonic acid (hereinafter abbreviated as "PFOS") and perfluorooctanoic acid (hereinafter abbreviated as "PFOA") are used as auxiliaries for fluororesin production. These organic fluoro-surfactants should not be discharged to the environment because they are stable and less degradable substances. In addition, organic fluoro-surfactants should preferably be recovered and reused as much as possible because they are expensive.

Some studies have been conducted on adsorbents capable of removing PFOS in water. Activated carbon is reported to be an effective adsorbent for removal of PFOS in water. However, activated carbon has such a disadvantage as it is difficult to be reused and enormous energy is necessary when adsorbed PFOS is recovered. In addition, when activated carbon is used in practical liquid waste treatment, adsorption efficiency goes down because activated carbon also has a high ability to adsorb organic substances other than PFOS.

Patent Document 1 reports that a cyclodextrin polymer derived from cyclodextrin is used as an adsorbent to adsorb and remove organic fluoro-compounds in water. It is, however, difficult to recover the adsorbed organic fluoro-compounds quantitatively or to reuse the adsorbent. There is still a high demand for improvements.

PRIOR ART DOCUMENT

Patent Document

Patent Document 1: Japanese Patent Laid-open Publication No. 2012-101159

SUMMARY OF INVENTION

Problems to be Solved by Invention

The present invention, which has been made in view of those circumstances, provides a material that is capable of selectively adsorbing organic fluoro-compounds such as perfluorooctane sulfonic acid, allows the adsorbed organic fluoro-compounds to be recovered, and is reusable as an adsorbent.

Solution to Problem

The present invention is directed to a polymer in which cyclodextrin is supported on the surface of a water-insoluble polymer, and to the use of the polymer as an adsorbent.

Effect of Invention

According to the present invention, there is provided a cyclodextrin-supported polymer material.

The cyclodextrin-supported polymer material of the present invention can selectively and efficiently adsorb organic fluoro-compounds such as organic fluoro-surfactants.

The adsorbed organic fluoro-compounds can be recovered from the cyclodextrin-supported polymer material of the present invention. After being recovered, the cyclodextrin-supported polymer material can be reused.

EMBODIMENTS FOR CARRYING OUT INVENTION

Figure 1:
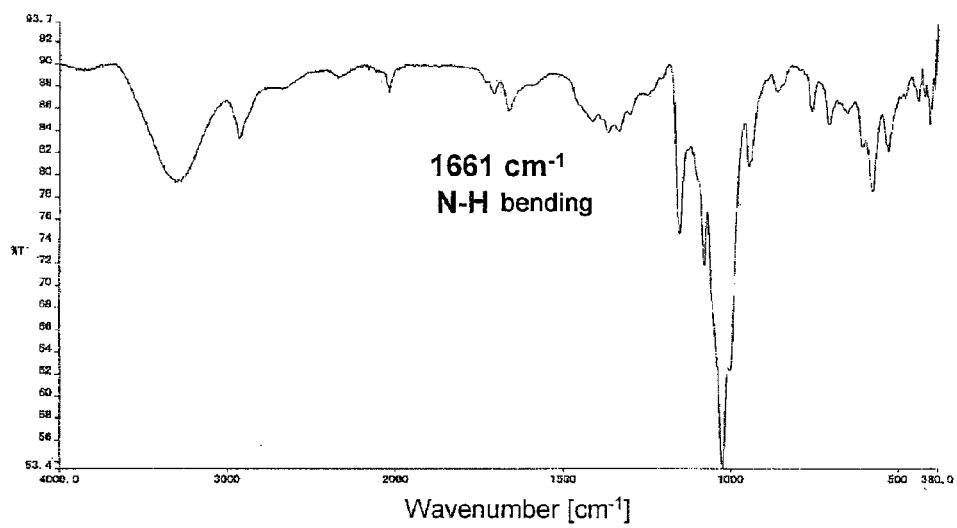
FIG. 1 is a chart of FT-IR spectrum of 6-amino-β-CD.

The cyclodextrin to be supported is a cyclodextrin (CD) that is a cyclic oligosaccharide represented by chemical formula (I) below in which six to eight glucose units are bonded.

[Chemical Formula 1]

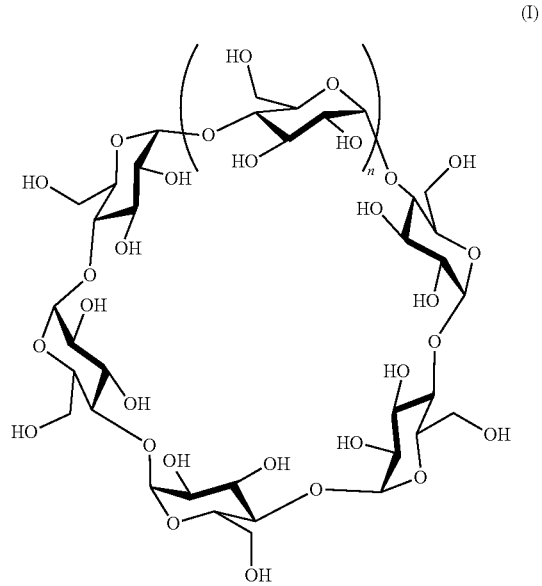

(I)

In the formula, n represents an integer of 1 to 3, preferably 1 to 2. When n is 1, 2, or 3, the cyclic oligosaccharide is called α-cyclodextrin (α-CD), β-cyclodextrin (β-CD), or γ-cyclodextrin (γ-CD), respectively.

A cyclodextrin is a plant-derived compound synthesized from starch using a CD synthase (cyclodextrin glucanotransferase) and has a nano-sized cavity as shown below.

[Chemical Formula 2]

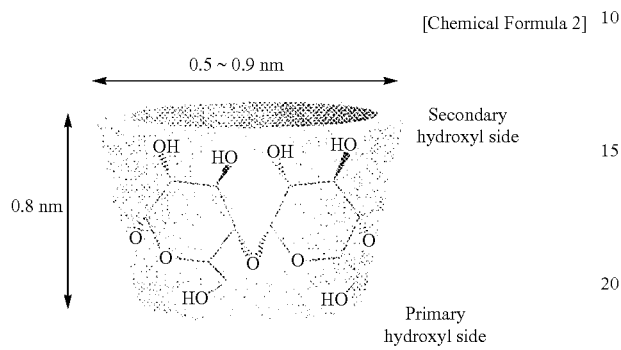

Each of α-cyclodextrin, β-cyclodextrin, and γ-cyclodextrin is commercially available from companies. For example, they are available in a pure form from Wako Pure Chemical Industries, Ltd., Tokyo Chemical Industry Co., Ltd., NACALAI TESQUE, INC., and Sigma-Aldrich.

The cyclodextrin may also be a dimer, trimer, or oligomer of a cyclodextrin as shown above, or a polymer thereof.

Examples of the water-insoluble polymer may include organic polymers such as polystyrene, polyester, polyamide, polyurethane, polyalkylene resins (polyethylene, polypropylene, etc.), polyacrylonitrile, polyvinyl chloride, polymethyl methacrylate, polycarbonate, polyacetal, polyether, polysaccharide, polypeptide, phenolic resin, urea resin, melamine resin, and epoxy resin, and copolymers thereof, fluoro-polymers such as polytetrafluoroethylene; inorganic polymers such as polysilane, polysiloxane, polysilsesquioxane, and polyphosphazene, and copolymers thereof; hybrids of any of various polymers shown above with an inorganic carrier such as silica gel, activated carbon or zeolite; and other water-insoluble materials. In the present invention, the term "water-insoluble" means substantially insoluble in water regardless of acidic or basic conditions.

The water-insoluble polymer may be in the form of particles, fibers, a nonwoven fabric, woven fabric, knitted web, a membrane, or the like, preferably in the form of particles. The form of the water-insoluble polymer may be appropriately selected depending on use. Porous particles can have a larger surface area and thus can be expected to be effective in adsorbing a larger amount of organic fluoro-compounds.

A reactive group is preferably present on or introduced on the surface of the polymer. For example, in the case of polystyrene, halogen atoms such as chlorine atoms may be introduced on the surface of polyethylene. Such introduction of halogen atoms can be performed by allowing polystyrene to react with formaldehyde and hydrogen chloride in the presence of an acid catalyst such as anhydrous zinc chloride. Commercial products such as polystyrene particles with a particle size of 35 to 74 μm (Merifield (trade name) manufactured by Sigma-Aldrich) are also available.

In the case of polyalkylene resin, halogen atoms such as chlorine atoms can be introduced using, for example, a compound having a reaction-active group to a polymerization initiator.

In the case of polyester, polyamide, polyurethane, or polyether, an active hydrogen-containing group such as a carboxyl group, a hydroxyl group, or an amino group may be used, which is present at the end of the polymer or in the skeleton of the polymer. In the other polymers, a reaction-active group such as active hydrogen in the molecule may also be used in the case of organic polymers such as polyacrylonitrile, polymethyl methacrylate, polycarbonate, polyacetal, polysaccharide, polypeptide, phenolic resin, urea resin, melamine resin, epoxy resin; and inorganic polymers such as polysilane, polysiloxane, polysilsesquioxane, polyphosphazene, and other inorganic polymers.

In view of cost, chemical stability, and insolubility in water, the polymer is preferably polystyrene, polymethyl methacrylate, or epoxy resin, in particular, polystyrene.

The present invention has a structure in which the cyclodextrin is supported on the surface of the above polymer. The term "structure . . . supported on" means that the polymer and the cyclodextrin are chemically bonded via a divalent linking group —X— wherein X represents N, O, S, $HN(CH_2)_nNH$ (n is 1 to 6, preferably 1 to 3), $O(CH_2)_nO$ (n is 1 to 6), or $O(CH_2CH_2O)_n$ (n is 2 to 6); the hyphen "-" represents a single bond; and X is preferably O or N, more preferably N.

For example, when β-cyclodextrin is supported on polystyrene particles, the processes can be carried out, for example, as follows.

The surface of polystyrene particles is subjected to chloromethylation. The chloromethylation can be performed, as mentioned above, by allowing polystyrene to react with formaldehyde and hydrogen chloride in the presence of an acid catalyst such as anhydrous zinc chloride. The degree of chloromethylation or chlorination is not restricted and may be appropriately set depending on use or purpose. Commercially available products include polystyrene particles (0.1 to 3 μm in average particle size, manufactured by Sigma-Aldrich), chloromethylated polystyrene (0.5 mmol/Cl/1 g to 4.5 mmol/Cl/1 g) with a particle size of 35 to 300 μm such as Merrifield's peptide resin (manufactured by Sigma-Aldrich), and porous or highly porous chloromethylated polystyrene (5.6 mmol/Cl/1 g) with a particle size of 50 to 300 μm manufactured by Mitsubishi Chemical Corporation.

On the other hand, β-cyclodextrin is subjected to amination. At least one of the OH groups present in the dextrin is aminated. This is because one amino group in the cyclodextrin is enough for the cyclodextrin to be bonded to and supported on polystyrene particles. Preferably, the OH group in position 3 or 6 outside the cavity of the cyclodextrin is aminated, and more preferably, the OH group in position 6 is aminated.

The amination of the cyclodextrin can be performed, for example, by converting the OH group of the cyclodextrin to a p-toluenesulfonyloxy group and then converting it to an amino group. Specifically, the OH group in position 6 can be converted to an amino group by tosylating the OH group with p-toluenesulfonyl chloride (tosylchloride), then converting the tosylated hydroxyl group to an azido group with sodium amide, and finally reducing the azido group with triphenylphosphine. Alternatively, the tosylated hydroxyl group can be more simply converted to an amino group by reaction with ammonia water. Other methods may also be used for the synthesis.

The chloromethylated polystyrene and the aminated cyclodextrin obtained as described above are subjected to a nucleophilic substitution reaction so that the cyclodextrin can be bonded to the polystyrene particles via an —NH-linkage. Specifically, this reaction can be performed by stirring the chloromethylated polystyrene and the aminated cyclodextrin in dimethylsulfoxide at 60° C. for 12 hours.

It is not necessary to bond cyclodextrin molecules to all the chloromethyl groups on the surface of polystyrene particles. Appropriate conditions may be selected depending on use or purpose.

Even when the polymer is the one other than polystyrene, the polymer can be chemically bonded to the cyclodextrin, for example, using an active hydrogen group, such as a carboxyl group, a hydroxyl group, or an amino group, present in the polymer or a reactive group (e.g., a halogen group such as a chloromethyl group) introduced to the polymer in combination with a reactive group (OH group) in the cyclodextrin or a reactive group (such as an —$NH_2$ group or an —SH group) formed by converting it in a manner modelling after the above case where the cyclodextrin is bonded to polystyrene particles.

The use of organic polymers is described. It will be understood, however, within the concept of the present invention that the polymer may be not only an organic polymer but also an inorganic polymer such as polysilane, polysiloxane, polysilsesquioxane and polyphosphazene; an inorganic material such as glass, silica gel, activated carbon and zeolite may also be used similarly. The present invention is intended to include cases where those materials are used.

The polymer according to the present invention in which the cyclodextrin is supported on the surface of the water-insoluble polymer may be used in combination with other adsorbents and/or other components, if necessary to form an organic fluoro-compound adsorbent.

The organic fluoro-compounds to be adsorbed include fluoroalkane carboxylic acids (R—COOH), fluoroalkane sulfonic acids (R—$SO_3H$), and fluoroalkyl alcohols (R—$(CH_2)_n$OH, wherein n is 1 to 6), in which at least one hydrogen atom is replaced by fluorine. R is $CF_3(CF_2)_n$ (n is 0 to 11), $HCF_2(CF_2)_n$ (n is 0 to 11), $CF_3(CF_2)_nO[CF(CF_3)CF_2O]_mCF(CF_3)$ (n is 0 to 5, and m is 0 to 5), or $(CF_3)_2CF(CF_2)_n$ (n is 0 to 10). Examples of the fluorolalkane carboxylic acids in which at least one hydrogen atom is replaced by fluorine include, but are not limited to, perfluoroalkane carboxylic acids such as perfluorobutanoic acid, perfluoropentanoic acid, perfluorohexanoic acid, perfluoroheptanoic acid, perfluorooctanoic acid, perfluorononanoic acid, perfluorodecanoic acid, perfluoroundecanoic acid, perfluorododecanoic acid, and perfluoro-2,5,8,-trimethyl-3,6,9-trioxadodecanoic acid; and hydrogen-containing fluoroalkane carboxylic acids such as 3H-tetrafluoropropionic acid, 5H-octafluorovaleric acid, 7H-dodecafluoroheptanoic acid, and 9H-hexadecafluorononanoic acid. In particular, the adsorbent has a high ability to adsorb perfluoropentanoic acid, perfluorohexanoic acid, perfluoroheptanoic acid, and perfluorooctanoic acid, especially, perfluoroheptanoic acid. Examples of the fluoroalkane sulfonic acids in which at least one hydrogen atom is replaced by fluorine include, but are not limited to, perfluoroalkane sulfonic acids such as perfluorobutane sulfonic acid, perfluorohexane sulfonic acid, and perfluorooctane sulfonic acids: and hydrogen-containing fluoroalkane sulfonic acids such as 6H-dodecafluoroheptane sulfonic acid and 8H-hexadecafluorooctane sulfonic acid. In particular, the adsorbent has a high ability to adsorb perfluorooctane sulfonic acid. Examples of the fluoroalkyl alcohols in which at least one hydrogen atom is replaced by fluorine include, but not limited to, 2-(perfluorobutyl)ethanol, 3-(perfluorobutyl)propanol, 6-(perfluorobutyl)hexanol, 2-(perfluorohexyl)ethanol, 3-(perfluorohexyl)propanol, 6-(perfluorohexyl)hexanol, 2-(perfluorooctyl)ethanol, 3-(perfluorooctyl)propanol, 6-(perfluorooctyl)hexanol, 2-perfluoropropoxy-2,3,3,3-tetrafluoropropanol, 1H, 1H-2,5-di(trifluoromethyl)-3,6-dioxaundecafluorononanol, 6-(perfluoro-1-methylethyl)hexanol, 2-(perfluoro-3-methylbutyl)ethanol, 1H,1H,5H-octafluoropentanol, 1H, 1H,7H-dodecafluoroheptanol, and 1H, 1H,9H-hexadecafluorononanol.

The removal of an organic fluoro-compound using the cyclodextrin-supported polymer can be performed by a process including the steps of:

adding the cyclodextrin-supported polymer to an aqueous solution containing the organic fluoro-compound; and bringing the cyclodextrin-supported polymer into contact with the organic fluoro-compound.

The organic fluoro-compound may be at any concentration as long as it is dissolved. An amount of the cyclodextrin-supported polymer to be added may be determined based on a content of the organic fluoro-compound and the amount of an aqueous solution. Some examples are performed using 0.1% by weight to 10% by weight of the cyclodextrin polymer as a standard amount per 1 ml of an aqueous solution containing 50 ppb to 1,000 ppm of the organic fluoro-compound.

The cyclodextrin-supported polymer used in the present invention has low miscibility with water-soluble solvents, in particular with water. Therefore, the organic fluoro-compound is adsorbed to the cyclodextrin in liquid-solid contact. To achieve such contact efficiently, a mixture of the aqueous solution containing the organic fluoro-compound and the cyclodextrin-supported polymer is usually stirred using known mixing means such as a magnetic stirrer.

The contact may be performed under room temperature (25° C.) and atmospheric pressure environment conditions for a time period of about 5 minutes to about 24 hours, although it depends on the means for contact. Some examples use a magnetic stirrer as the mixing means and the following conditions: pressure, atmospheric pressure; temperature, 25° C. (room temperature); stirring time, 1 hour.

After the contact step, the cyclodextrin-supported polymer is separated from the aqueous solution by filtration. The separated aqueous solution filtrate is the one in which an organic fluoro-compound is removed from the aqueous solution containing the organic fluoro-compound before the cyclodextrin-supported polymer is added. Whether or not the organic fluoro-compound is removed can be checked by analyzing, by LC-MS-MS, the aqueous solution obtained by removal of the cyclodextrin-supported polymer and calculating the removal rate.

In the present invention, the adsorption removal efficiency varies depending on the type or concentration of the organic fluoro-compound contained, the amount of the aqueous solution containing the compound, the type or amount of the cyclodextrin-supported polymer used, or the mixing method. The contact may be performed not only once but twice or more, in other words, the aqueous solution containing the organic fluoro-compound may be brought into contact with a large amount of the cyclodextrin-supported polymer, so that theoretically, the organic fluoro-compound can be removed by almost 100%. It has been found that about 0.1 to 1 mole of an organic fluoro-compound can be adsorbed per 1 mole of cyclodextrin. Therefore, a specific adsorption process may be designed with reference to this information.

The cyclodextrin-supported polymer separated by filtration may be washed with a polar solvent such as ethanol or acetone, so that the adsorbed organic fluoro-compound can be separated from the cyclodextrin-supported polymer. The cyclodextrin-supported polymer can be reused in the method of the present invention after washed with water. The organic fluoro-compound can be recovered in the form of a highly concentrated liquid and subjected to a suitable decomposition process or reused.

Some reactive groups (such as chloromethyl groups) left on the polymer surface without being used for supporting cyclodextrin may be modified with a functional group other than cyclodextrin. In the above case, for example, the chloro group of the chloromethyl group left without being used for the supporting reaction may be converted to a dimethylamino group. The conversion to such a group makes it possible to increase the initial ability to adsorb the organic fluoro-compound. The conversion to another functional group such as an amino, hydroxyl, thiol, carboxyl, amide, urea, alkylether, or fluoroalkylether group allows secondary interaction with the organic fluoro-compound on the polymer surface in addition to the adsorption ability of cyclodextrin.

A specific example of use may include such a system assembled by filling a column with the cyclodextrin-supported particles of the present invention and allowing organic fluoro-surfactant-containing waste water to pass through the column, which makes it possible to treat a large amount of waste water in a short time without environmental loading. The waste water may be circulated so that the adsorption efficiency can be increased.

After used, the adsorbent filled column may be washed with a polar solvent, so that the organic fluoro-surfactant can be recovered in a small amount of highly concentrated liquid and the adsorbent can be reused in the next waste water treatment.

The system assembled as described above to remove and recover the organic fluoro-surfactant using the cyclodextrin-supported particles of the present invention makes it possible to quickly separate and recover the organic fluoro-surfactant from environmental water in an energy-saving manner, which can significantly contribute to, for example, all removal of organic fluoro-surfactants in the environment.

EXAMPLES

Synthesis of 6-amino-β-CD

Under a nitrogen atmosphere, a solution of sodium azide (0.10 g, 1.6 mmoL) dissolved in deionized water (10 mL) was added to 6-tosylated-β-CD (manufactured by Tokyo Chemical Industry Co., Ltd.) (0.10 g, 0.078 mmoL) and then allowed to react at 100° C. overnight. After cooling to room temperature, the precipitate was removed by filtration, and at least 90% of water was removed from the resultant filtrate by distillation under reduced pressure. Extraction was performed by adding 1,1,2,2-tetrachloroethane (5 mL), and the resultant organic layer was concentrated to give a white solid. The white solid was recrystallized from water (quantity 0.037 g, yield 41%). The resultant 6-azido-β-CD (0.029 g, 0.025 mmol) and triphenylphosphine (7.5 mg, 0.0275 mmoL) were dissolved in dimethylformamide (1 mL) and stirred at room temperature for 2 hours. Subsequently, 0.1 mL of deionized water was added to the mixture and stirred at 90° C. for 3 hours. After cooling to room temperature, 10 mL of acetone was added to the reaction mixture, and the resultant precipitate was separated by filtration. The precipitate was washed with acetone and then dried under vacuum to give 6-amino-β-CD (quantity 0.028 g, yield 98%).

Alternatively, 50 mL of 28% ammonium water was added to 6-tosylated-β-CD (10 g, 7.8 mmol) and allowed to react at 50° C. for 12 hours. Subsequently, the reaction mixture was cooled to room temperature and then poured into 500 mL of acetone. The resultant precipitate was separated by filtration and then dried, so that 6-amino-β-CD (8.8 g, yield 100%) was also successfully obtained.

FIG. 1 shows the infrared absorption (FT-IR) spectrum of the product.

The FT-IR spectrum showed absorption at 1,661 cm$^{-1}$ for the N—H bending vibration of the primary amino group. Thereby, the production of 6-amino-β-CD was confirmed.

Chloromethylated Polystyrene Particles

Chloromethylated polystyrene particles (Merrifield's peptide resin manufactured by Sigma Aldrich) were used (particle size 35-74 μm, 3.5-4.5 mmol/Cl/1 g).

Synthesis of β-CD-supported Polystyrene Particles (PS-N-β-CD)

[Chemical Formula 3]

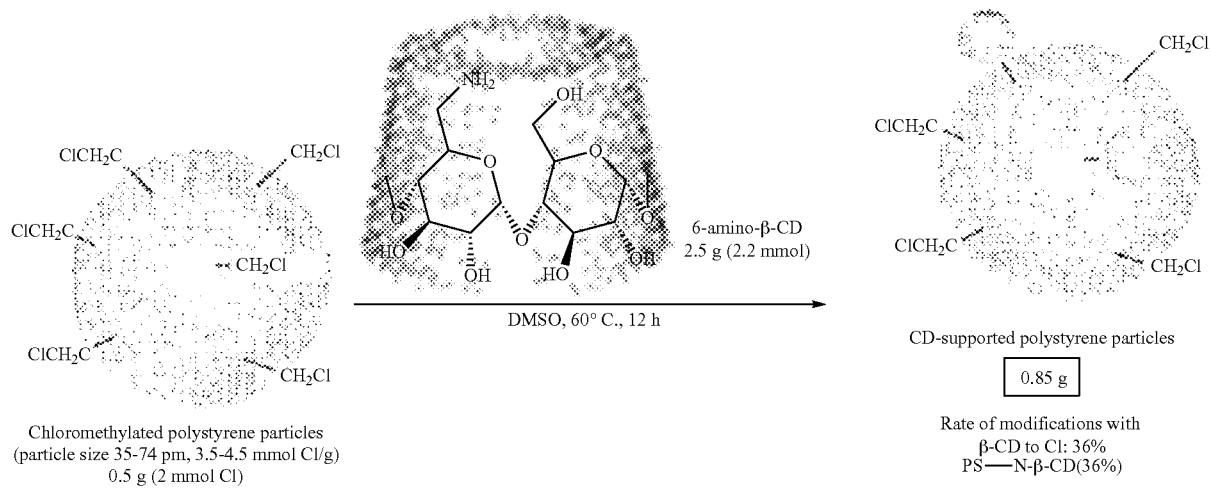

To a dimethylsulfoxide (DMSO) solution containing 2.5 g (2.2 mmol) of the obtained 6-amino-β-CD was added 0.5 g (2 mmol Cl) of the chloromethylated polystyrene particles (PS-CH$_2$Cl particles) and stirred at 60° C. for 12 hours.

The polystyrene particles-containing DMSO solution was then subjected to filtration, so that 0.85 g of CD-supported polystyrene particles (PS-N-β-CD particles) were obtained.

Figure 2:
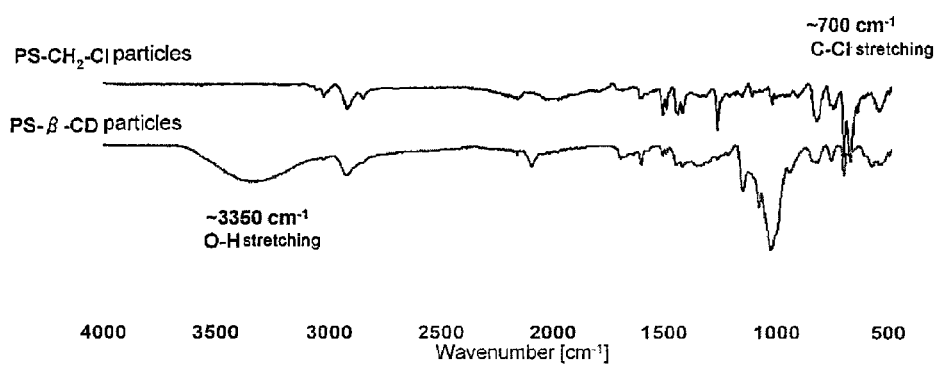
FIG. 2 is a chart of FT-IR spectra of PS-CH$_2$Cl particles and PS-N-β-CD particles.

FIG. 2 shows the FT-IR spectrum of the resultant particles together with that of the chloromethylated polystyrene particles. The PS-N-β-CD particles) showed that the intensity of the absorption for the C—Cl stretching vibration (about 700 cm$^{-1}$) of the chloromethyl group is lower in the spectrum of the PS-N-β-CD particles than in that of the chloromethylated polystyrene particles. On the other hand, a new absorption for the O—H stretching vibration of the CD hydroxyl group is observed at 3,350 cm$^{-1}$. It is, therefore, understood that 6-amino-β-CD is immobilized on the chloromethylated polystyrene particles.

The rate of modification with β-CD to Cl was 36%. The resultant particles are named "PS-N-β-CD (36%)."

The rate of modification with β-CD to Cl was calculated from the amount of consumption of Cl using the elemental analysis values of the chloromethylated polystyrene particles and the resultant PS-N-β-CD.

β-CD-supported polystyrene particles were prepared to obtain β-CD-supported polystyrene particles with a rate of β-CD modification to Cl of 6% (PS-N-β-CD (6%)) in the same manner as in the PS-N-β-CD (36%) preparation method, except that the added amount of 6-amino-β-CD in the production of PS-N-β-CD (36%) was changed to 0.91 g (0.8 mmol).

Evaluation of Ability of β-CD-supported Polystyrene Particles (PS-N-β-CD) to Adsorb Organic Fluoro-Compound (50 Ppb)

[Chemical Formula 4]

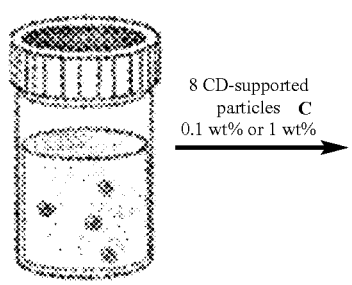

Water (10 mL)
containing PFHxA,
PFOA, and PFOS
(each 50 ppb)

8 CD-supported
particles C
0.1 wt% or 1 wt%

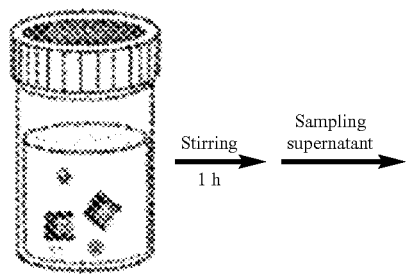

Stirring
1 h

Sampling
supernatant

-continued

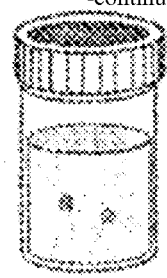

Calculating adsorption
rate from HPLC
measurements of
PFHeA concentration

The obtained β-CD-supported polystyrene particles (PS-N-β-CD (36%) and PS-N-β-CD (6%)) were added at 0.1% by weight and 1% by weight (based on the weight of water) respectively to 10 ml (pH 8) of an aqueous solution containing 50 ppb of each of perfluorohexanoic acid (PFHxA), perfluorooctanoic acid (PFOA), and perfluorooctane sulfonic acid (PFOS), and stirred with a magnetic stirrer at room temperature for 1 hour.

Subsequently, the supernatant was sampled and subjected to high-performance liquid chromatography (HPCL). The concentration of the remaining organic fluoro-compound in the supernatant was measured by HPLC, and the amount of the organic fluoro-compound removed by the adsorption (adsorption rate) was determined from the measured concentration as follows.

The adsorbed amount (g) was calculated as {50−concentration (ppb) of remaining organic fluoro-compound}×10$^{-8}$.

The adsorption rate was calculated as {50−concentration (ppb) of remaining organic fluoro-compound}50×100.

For comparison, the ability of the chloromethylated polystyrene particles (PS-Cl) with no β-CD supported thereon to adsorb organic fluoro-compounds was evaluated in the same manner.

Figure 3:
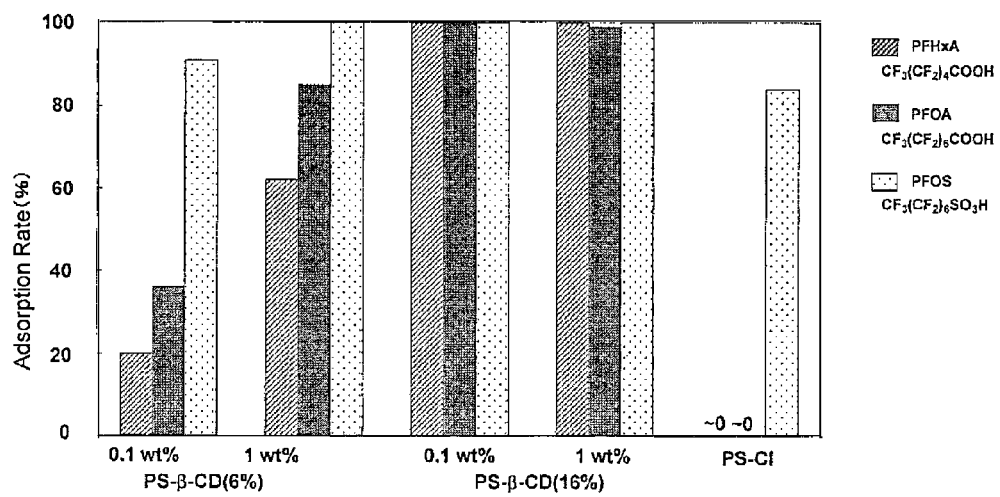
FIG. 3 is a graph showing results of evaluation of adsorption to PS-N-β-CD particles and PS-CH$_2$Cl particles.

FIG. 3 shows the results of the evaluation.

FIG. 3 shows that the rate of adsorption of the organic fluoro-compounds was almost 100% in both cases where PS-N-β-CD (36%) particles with the rate of β-CD modification to Cl of 36% were added at concentrations of 0.1% by weight and 1% by weight. On the other hand, in the case of PS-N-β-CD (6%) particles with the β-CD modification rate of 6%, the adsorption rate significantly decreased as the addition rate decreased. This indicates that β-CD on the polystyrene surface contributes to the adsorption of organic fluoro-compounds. The reason why PS-Cl adsorbs PFOS is that PFOS is more likely to be adsorbed to a carrier having a hydrophobic surface and thus can connect with the hydrophobic surface of PS-Cl by hydrophobic interaction.

Evaluation of Ability of β-CD-supported Polystyrene Particles (PS-N-β-CD (36%)) to Adsorb Organic Fluoro-compound (PFHxA) (1,000 ppm)

[Chemical Formula 5]

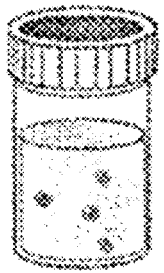

β-CD-supported
particles
1 wt% or 10 wt%

Water (1 mL)
containing PFHxA
(1,000 ppm)

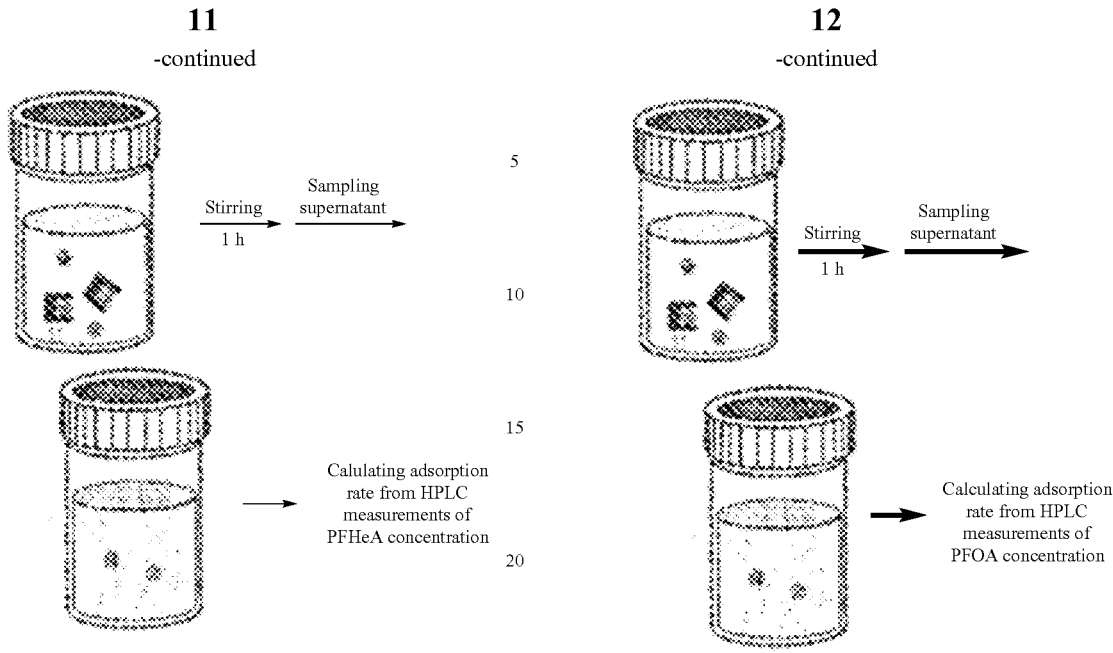

The obtained β-CD-supported polystyrene particles (PS-N-β-CD (36%)) were added at 1% by weight and 10% by weight (based on the weight of water) respectively to 1 ml of an aqueous solution (pH 2.5, 7, or 10) containing 1,000 ppm of perfluorohexanoic acid (PFHxA), and stirred with a magnetic stirrer at room temperature for 1 hour. The pH of the aqueous PFHxA solution was adjusted by adding a suitable amount of sodium hydroxide to the aqueous solution.

Subsequently, the supernatant was sampled and subjected to high-performance liquid chromatography (HPCL). The concentration of the remaining organic fluoro-compound in the supernatant was measured, and the amount of the organic fluoro-compound removed by the adsorption was determined from the measured concentration.

Figure 4:
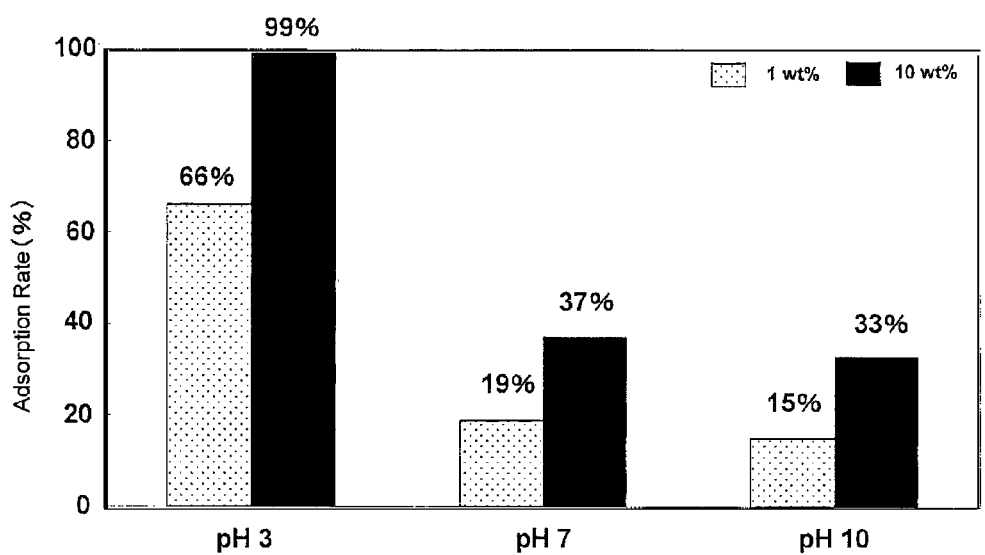
FIG. 4 is a graph showing evaluation of ability of PS-N-β-CD particles to adsorb PFHxA (1,000 ppm).

FIG. 4 shows the results of the evaluation.

FIG. 4 indicates that the ability of the β-CD-supported polystyrene particles to adsorb PFHxA is influenced by pH of the aqueous solution and higher in the acidic aqueous solution than in the neutral or alkaline aqueous solution. It is conceivable that the adsorption ability is increased in an acidic aqueous solution by electrostatic interaction between the amino group (ammonio group) in position 6 of β-CD and the carboxyl group of PFHxA in addition to inclusion of the fluorocarbon chain of PFHxA in the cavity of β-CD.

Evaluation of Ability of β-CD-supported Polystyrene Particles (PS-N-β-CD (36%)) to Adsorb Organic Fluoro-Compound (PFOS) (1,000 Ppm)

[Chemical Formula 6]

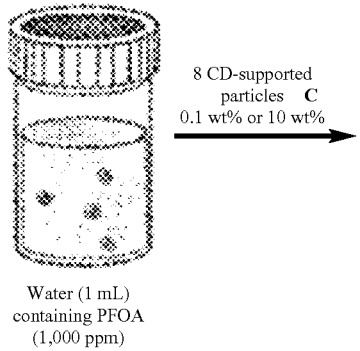

Water (1 mL) containing PFOA (1,000 ppm)

8 CD-supported particles C
0.1 wt% or 10 wt%

The obtained β-CD-supported polystyrene particles (PS-N-β-CD (36%)) were added at 1% by weight and 10% by weight (based on the weight of water) respectively to 1 ml of an aqueous solution (pH 3, 7, or 10) containing 1,000 ppm of perfluorooctanoic acid (PFOA), and stirred with a magnetic stirrer at room temperature for 1 hour. The pH of the aqueous PFHxA solution was adjusted by adding a suitable amount of sodium hydroxide to the aqueous solution.

Subsequently, the supernatant was sampled and subjected to high-performance liquid chromatography (HPCL). The concentration of the remaining organic fluoro-compound in the supernatant was measured, and the amount of the organic fluoro-compound removed by the adsorption was determined from the measured concentration.

Figure 5:
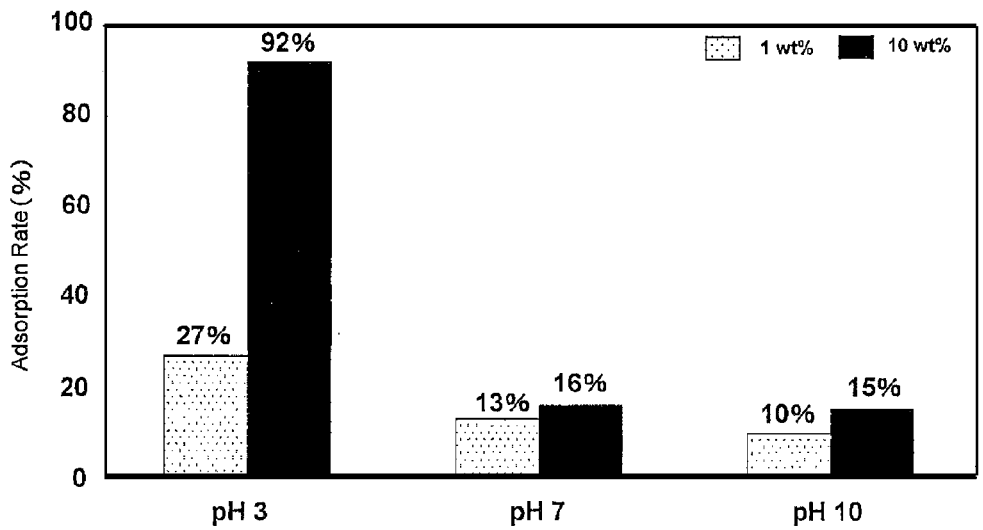
FIG. 5 is a graph showing evaluation of ability of PS-N-β-CD particles to adsorb PFOS (1,000 ppm).

FIG. 5 shows the results of the evaluation.

FIG. 5 indicates that the ability of the β-CD-supported polystyrene particles to adsorb PFOA is also influenced by pH of the aqueous solution and higher in the acidic aqueous solution than in the neutral or alkaline aqueous solution. It is conceivable that as in the case of PFHxA, the adsorption ability is increased in an acidic aqueous solution by electrostatic interaction between the amino group (ammonio group) in position 6 of β-CD and the carboxyl group of PFOA in addition to inclusion of the fluorocarbon chain of PFOA in the cavity of β-CD.

Recovery of PFHxA from β-CD-supported Polystyrene Particles

[Chemical Formula 7]

Adsorption experiment
PFHxA (C6): 1,000 ppm
(1 mg/1 mL)
8 CD-supported particles:
10 or 100 mg
350 rpm, 1 h, r.t.

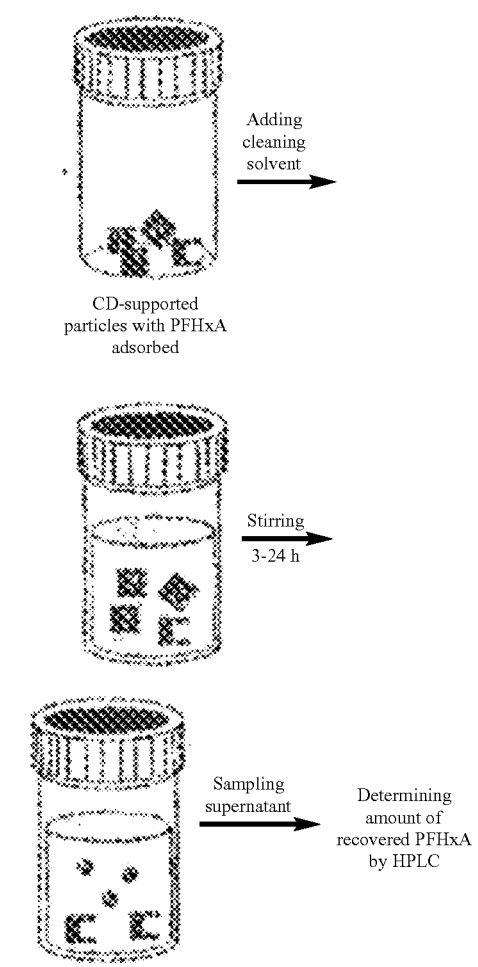

CD-supported particles with PFHxA adsorbed

Adding cleaning solvent →

Stirring 3-24 h

Sampling supernatant → Determining amount of recovered PFHxA by HPLC

The obtained β-CD-supported polystyrene particles (PS-N-β-CD (36%)) were added at 1% by weight and 10% by weight (based on the weight of water) respectively to 1 ml of an aqueous solution (pH 2.5) containing 1,000 ppm of perfluorohexanoic acid (PFHxA), and stirred with a magnetic stirrer at 350 rpm at room temperature for 1 hour.

The supernatant was sampled and subjected to high-performance liquid chromatography (HPCL). The concentration of the remaining organic fluoro-compound in the supernatant was measured, and the amount of the organic fluoro-compound removed by the adsorption was determined from the measured concentration.

The β-CD-supported polystyrene particles (PS-N-β-CD (36%)) adsorbing PFHxA were separated from the solution, then added to 1 ml of a cleaning solvent, and stirred with a magnetic stirrer for 3 to 24 hours.

Subsequently, the supernatant was sampled and subjected to high-performance liquid chromatography (HPLC). The concentration of PFHxA dissolved in the supernatant was measured and an amount of recovered PFHxA was calculated as follows.

The recovered amount was calculated based on (concentration of PFHxA dissolved in supernatant) (mg/mL)×1 mL.

Table 1 shows the above conditions and the recovered amounts.

TABLE 1

| Cleaning solvent | Adsorbent amount | Amount of adsorbed PFHxA | Stirring time | Amount of recovered PFHxA (recovery rate) |
|---|---|---|---|---|
| Acetone (1 mL) | 10 mg | 0.65 mg | 3 h | 0.10 mg (15%) |
|  |  |  | 15 h | 0.21 mg (31%) |
|  |  |  | 24 h | 0.31 mg (47%) |
| Acetone (1 mL) | 100 mg | 1.0 mg | 3 h | 0.88 mg (88%) |
|  |  |  | 15 h | 0.96 mg (96%) |
|  |  |  | 24 h | 1.00 mg (100%) |
| 2-propanol (1 mL) | 10 mg | 0.67 mg | 3 h | 0.08 mg (13%) |
|  |  |  | 10 h | 0.10 mg (15%) |
|  |  |  | 24 h | 0.27 mg (40%) |
| Acetonitrile (1 mL) | 10 mg | 0.72 mg | 3 h | 0.05 mg (8%) |
|  |  |  | 10 h | 0.07 mg (10%) |
|  |  |  | 24 h | 0.17 mg (24%) |

Table 1 shows that PFHxA can be almost completely recovered using acetone as a cleaning solvent and that the lower the content (% by weight) of PFHxA in the adsorbent, the higher the recovery rate obtained by acetone cleaning.

Synthesis 1 of β-CD-supported Polystyrene Particles (PS-O-β-CD)

[Chemical Formula 8]

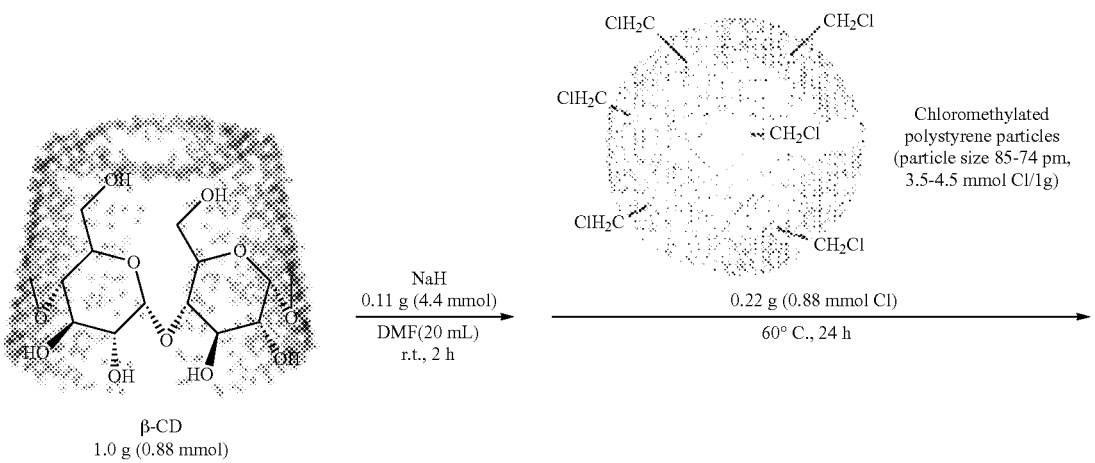

β-CD
1.0 g (0.88 mmol)

NaH
0.11 g (4.4 mmol)
DMF(20 mL)
r.t., 2 h 0.22 g (0.88 mmol Cl)
60° C., 24 h

Chloromethylated polystyrene particles (particle size 85-74 pm, 3.5-4.5 mmol Cl/1g)

-continued

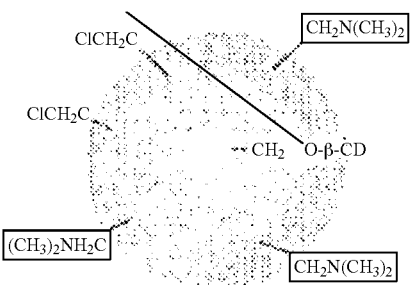

CD-supported polystyrene particles 0.26 g

β-CD modification rate: 4%
(calculated from weight change)

DMF: $(CH_3)_2N—CH=O$

In 20 ml of DMF were dissolved 1.0 g (0.88 mmol) of β-CD (manufactured by Tokyo Chemical Industry Co., Ltd.) and 0.11 g (4.4 mmol) of NaH and stirred at room temperature for 2 hours. To the resultant solution was added 0.22 g (0.88 mmol Cl) of chloromethylated polystyrene particles (particle size: 35-74 μm, chlorine content: 3.5-4.5 mmol Cl/1 g) and stirred with a magnetic stirrer at 60° C. for 24 hours.

Figure 6:
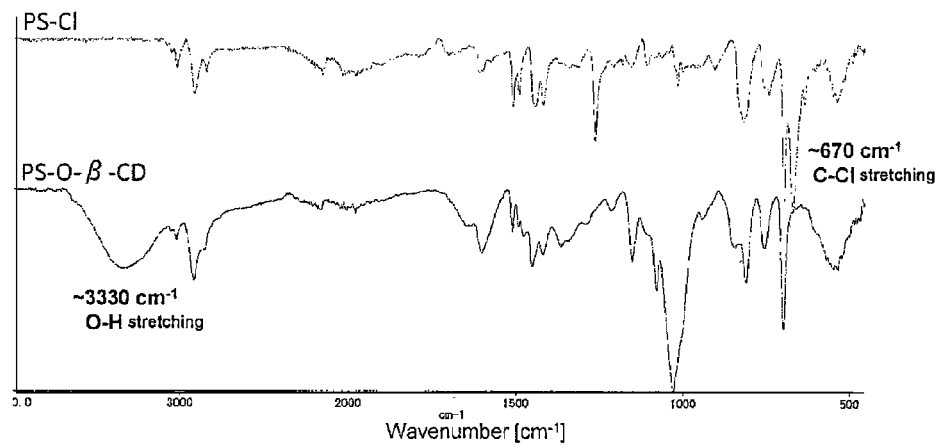
FIG. 6 is a chart of FT-IR spectra of PS-CH$_2$Cl particles and PS-O-β-CD particles.

FIG. 6 shows the FT-IR spectrum of the obtained particles together with that of the chloromethylated polystyrene particles. The intensity of the absorption for the C—Cl stretching vibration (about 670 cm$^{-1}$) of the chloromethyl group is lower in the spectrum of the PS-N-β-CD particles than in that of the chloromethylated polystyrene particles. On the other hand, new absorption for the O—H stretching vibration of the CD hydroxyl group is observed at 3,330 cm$^{-1}$. It is, therefore, understood that β-CD is immobilized on the chloromethylated polystyrene particles.

The rate of modification with β-CD to Cl was 4%. The resultant particles are named "PS-O-β-CD (4%)."

The rate of modification with β-CD to Cl was calculated from the weight increase obtained by subtracting the weight of the chloromethylated polystyrene particles before the reaction from the weight of the CD-supported polystyrene particles obtained after the reaction.

Evaluation of Ability of β-CD-supported Polystyrene Particles (PS-O-β-CD (4%)) to Adsorb Organic Fluoro-Compound (PFHxA) (1,000 Ppm)

[Chemical Formula 9]

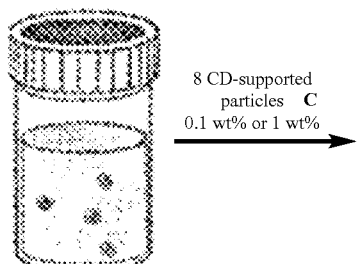

Water (1 mL)
containing PFHeA
(1,000 ppm)

8 CD-supported
particles C
0.1 wt% or 1 wt%

-continued

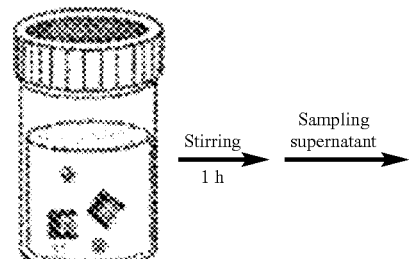

Stirring
1 h

Sampling
supernatant

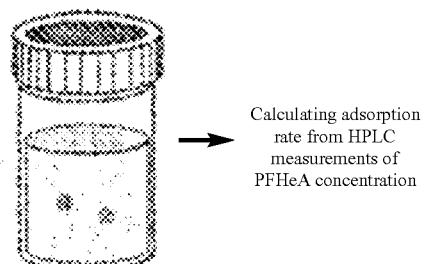

Calculating adsorption
rate from HPLC
measurements of
PFHeA concentration

The obtained β-CD-supported polystyrene particles (PS-O-β-CD (4%)) were added at 0.1% by weight and 1% by weight (based on the weight of water) respectively to 1 ml of an aqueous solution (pH 2.5) containing 1,000 ppm of perfluorohexanoic acid (PFHxA), and stirred with a magnetic stirrer at room temperature for 1 hour.

Subsequently, the supernatant was sampled and subjected to high-performance liquid chromatography (HPCL). The concentration of the remaining organic fluoro-compound in the supernatant was measured, and the amount of the organic fluoro-compound removed by the adsorption was determined from the measured concentration.

For reference purpose, the ability of quaternary ammonium salt-type strong base anion exchange resin (IER) to adsorb PFHxA (1,000 ppm) was evaluated in the same manner as described above.

Figure 7:
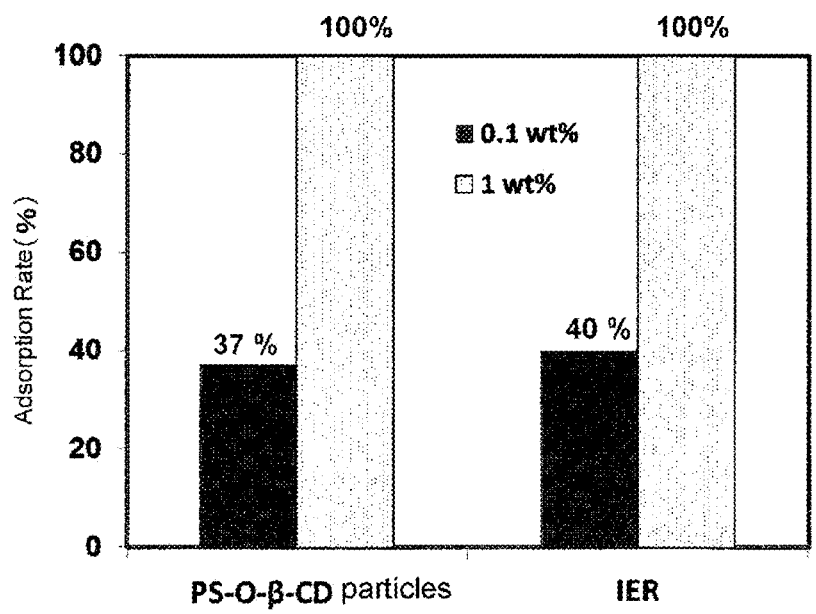
FIG. 7 is a graph showing results of evaluation of adsorption to PS-O-β-CD particles and IER particles.

FIG. 7 shows the results. It is understood from FIG. 7 that PS-O-β-CD has substantially the same ability to adsorb PFHxA as the strong base anion exchange resin.

Synthesis of β-CD-supported Polystyrene Particles (PS-O-β-CD) (3%)

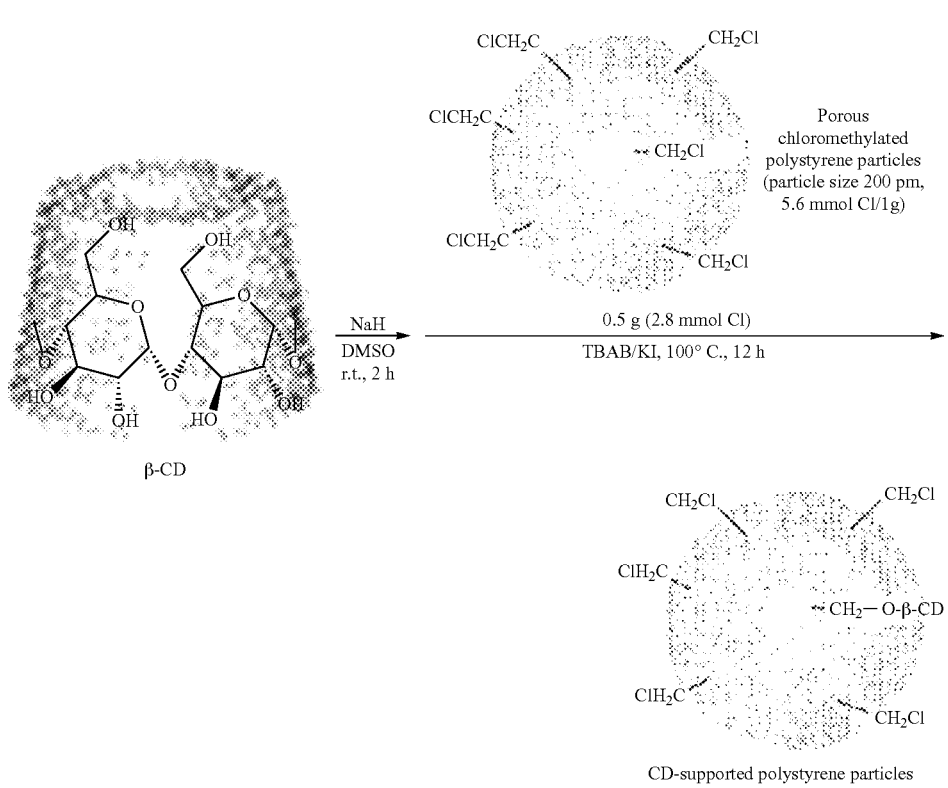

[Chemical Formula 10]

In 170 mL of DMSO were dissolved 7.0 g (6.2 mmol) of β-CD (manufactured by Tokyo Chemical Industry Co., Ltd.) and 1.24 g (31 mmol) of NaH and stirred at room temperature for 2 hours. To the resultant solution were added 2.2 g (6.8 mmol) of tetra-n-butylammonium bromide, 0.68 g (4.0 mmol) of potassium iodide, and 0.5 g (2.8 mmol Cl) of chloromethylated polystyrene particles (particle size: 200 μm, chlorine content: 5.6 mmol Cl/1 g) and stirred with a magnetic stirrer at 100° C. for 12 hours.

Subsequently, the polystyrene particle-containing DMSO solution was subjected to filtration to give 0.576 g of CD-supported polystyrene particles (PS-O-β-CD).

Figure 8:
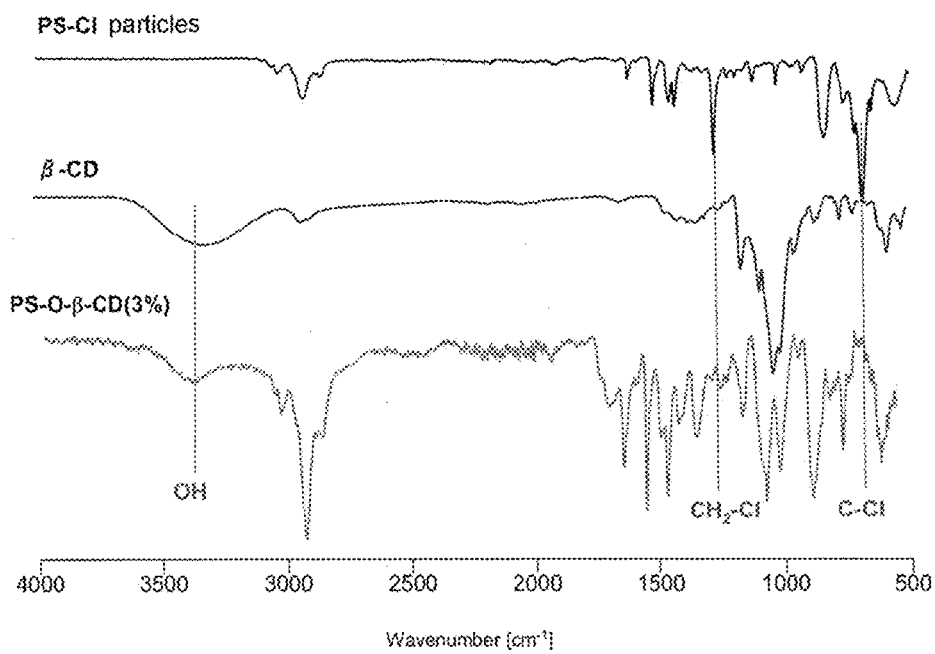
FIG. 8 is a chart of FT-IR spectra of PS-CH$_2$Cl particles, β-CD, and PS-O-β-CD particles.

FIG. 8 shows the FT-IR spectrum of the resultant particles together with those of the chloromethylated polystyrene particles and β-CD. The intensity of the absorption for the C—Cl stretching vibration (about 670 cm$^{-1}$) of the chloromethyl group is lower in the spectrum of the resultant particles than in that of the chloromethylated polystyrene particles. On the other hand, new absorption for the O—H stretching vibration of the CD hydroxyl group is observed at 3,330 cm$^{-1}$. It is therefore understood that β-CD is immobilized on the chloromethylated polystyrene particles.

The rate of modification with β-CD to Cl was 3%. The resultant particles are named "PS-O-β-CD (3%)."

The rate of modification with β-CD to Cl was calculated from the weight increase obtained by subtracting the weight of the chloromethylated polystyrene particles before the reaction from the weight of the CD-supported polystyrene particles obtained after the reaction.

Evaluation of Ability of β-CD-supported Polystyrene Particles (PS-O-β-CD (3%)) to Adsorb Organic Fluoro-Compound (PFHxA) (1,000 ppm)

[Chemicak Formula 11]

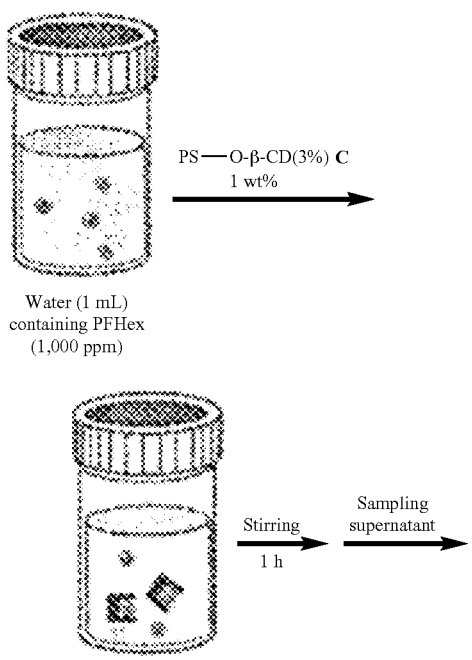

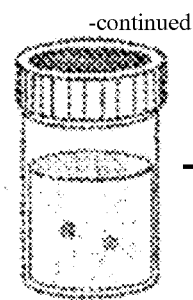

Calculating adsorption rate from HPLC measurements of PFHeA concentration

The obtained β-CD-supported polystyrene particles (PS-O-β-CD (3%)) were added at 1% by weight (based on the weight of water) to 1 mL of an aqueous solution (pH 2.5) containing 1,000 ppm of perfluorohexanoic acid (PFHxA), and stirred with a magnetic stirrer at room temperature for 1 hour.

Subsequently, the supernatant was sampled and subjected to high-performance liquid chromatography (HPCL). The concentration of the remaining organic fluoro-compound in the supernatant was measured, and the amount of the organic fluoro-compound removed by the adsorption was determined from the measured concentration.

Synthesis of 6-mono-(N-aminoethyl)amino-β-CD

Under a nitrogen atmosphere, dimethylformamide (3 mL) and ethylenediamine (2.5 mL, 37.4 mmol) were added to 6-tosylated-β-CD (manufactured by Tokyo Chemical Industry Co., Ltd.) (1.0 g, 0.78 mmol) and then reaction was performed at 65° C. for 3 hours. After cooled to room temperature, the reaction mixture was added to 100 mL of acetone. The resultant precipitate was separated by filtration. The precipitate was washed with acetone and then dried under vacuum to give 6-mono-(N-aminoethyl)amino-β-CD (quantity 0.80 g, yield 87%).

Figure 9:
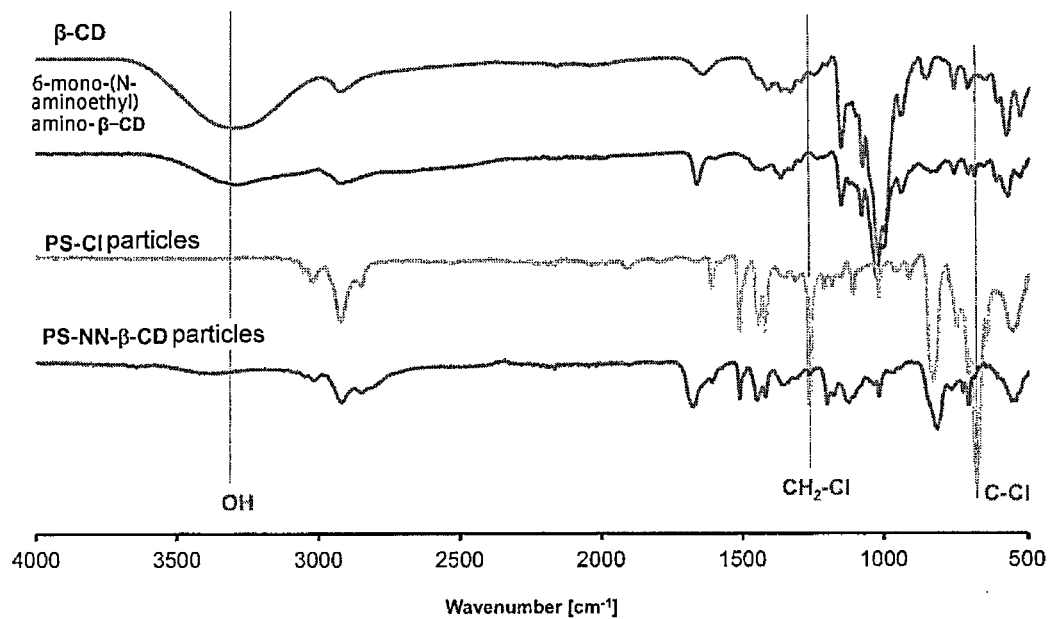
FIG. 9 is a chart of FT-IR spectra of β-CD, 6-mono-(N-aminoethyl)amino-β-CD, PS-CH$_2$Cl particles, and PS-NN-β-CD particles.

FIG. 9 shows the infrared absorption spectrum of the product.

The FT-IR spectrum showed an absorption at 1,673 $cm^{-1}$ for the N—H bending vibration of the primary amino group, which showed the production of 6-mono-(N-aminoethyl)amino-β-CD.

Synthesis of β-CD-supported Polystyrene Particles (PS-NN-β-CD)

[Chemical Formula 12]

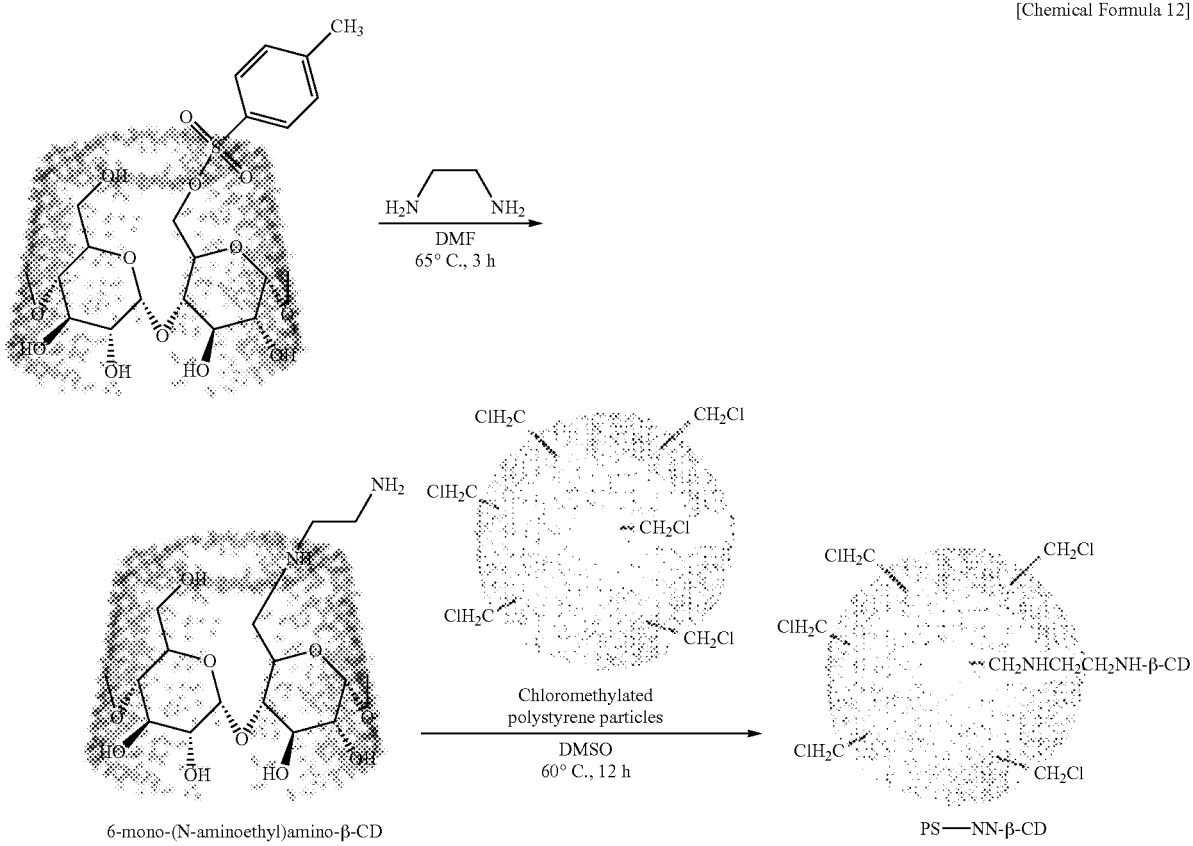

To a dimethylsulfoxide (DMSO) solution containing 0.47 g (0.4 mmol) of the obtained 6-mono-(N-aminoethyl)amino-β-CD was added 0.050 mg (0.28 mmol Cl) of chloromethylated polystyrene particles (PS-CH₂Cl particles) (particle size: 200 μm, chlorine content: 5.6 mmol Cl/1 g) and stirred at 60° C. for 12 hours.

The polystyrene particle-containing DMSO solution was then subjected to filtration to give 0.051 g of CD-supported polystyrene particles (PS-NN-β-C) particles).

FIG. 9 shows the FP-IR spectrum of the resultant particles together with that of the chloromethylated polystyrene particles. The intensity of the absorption for the C—Cl stretching vibration (about 700 $cm^{-1}$) of the chloromethyl group is lower in the spectrum of the PS-NN-β-CD particles than in that of the chloromethylated polystyrene particles. On the other hand, new absorption for the O—H stretching vibration of the CD hydroxyl group is observed at 3,474 cm$^{-1}$. It is, therefore, understood that that 6-mono-(N-aminoethyl) amino-β-CD is immobilized on the chloromethylated polystyrene particles.

The rate of modification with β-CD to Cl was 34%. The resultant particles are named "PS-NN-β-CD."

The rate of modification with β-CD to Cl was calculated from the weight increase obtained by subtracting the weight of the chloromethylated polystyrene particles before the reaction from the weight of the CD-supported polystyrene particles obtained after the reaction.

Evaluation of Ability of β-CD-supported Polystyrene Particles (PS-NN-β-CD) to Adsorb Organic Fluoro-Compound (PFHxA) (1,000 Ppm)

[Chemical Formula 13]

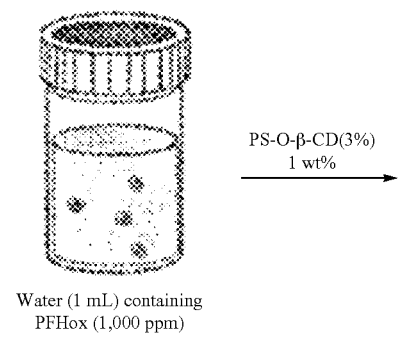

Water (1 mL) containing PFHox (1,000 ppm)

PS-O-β-CD(3%)
1 wt%

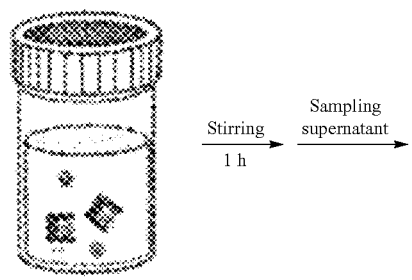

Stirring
1 h

Sampling supernatant

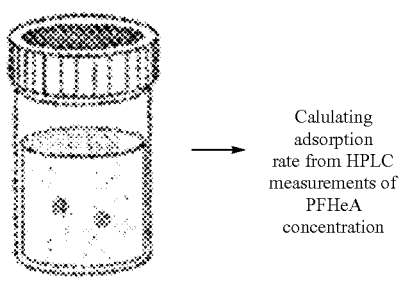

Calulating adsorption rate from HPLC measurements of PFHeA concentration

The obtained β-CD-supported polystyrene particles (PS-NN-β-CD) were added at 0.1 or 1% by weight based on the weight of water to 1 mL of an aqueous solution (pH 2.5) containing 1.000 ppm of perfluorohexanoic acid (PFHxA), and stirred with a magnetic stirrer at room temperature for 1 hour.

Figure 10:
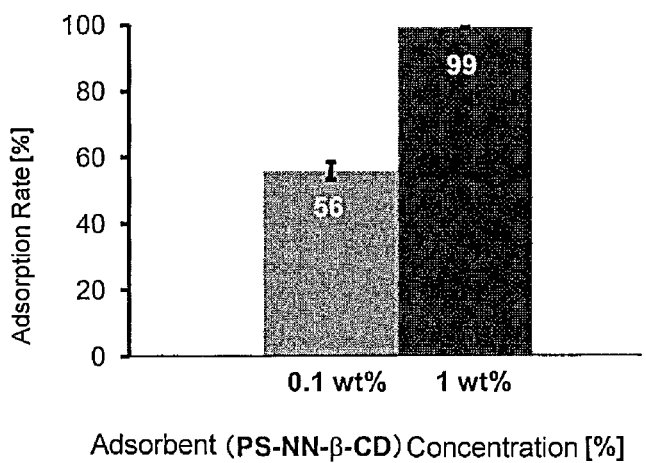
FIG. 10 is a graph showing amount of organic fluoro-compound adsorbed on PS-NN-β-CD.

Subsequently, the supernatant was sampled and subjected to high-performance liquid chromatography (HPCL). The concentration of the remaining organic fluoro-compound in the supernatant was measured, and the amount of the organic fluoro-compound removed by the adsorption was determined from the measured concentration. FIG. 10 shows the results.

Comparative Example

According to paragraphs 0045 to 0046 of Patent Document 1, a cyclodextrin polymer was synthesized by reaction of 4,4'-methylene-bis(phenylene isocyanate) with 2,6-di-o-methyl-β-cyclodextrin.

That is, under a nitrogen atmosphere, 4,4'-methylene-bis(phenylene isocyanate) (504 mg, 2.25 mmol) and 2,6-di-o-methyl-β-cyclodextrin (1.00 g, 7.51×10$^{-1}$ mmol) were dissolved in 10 mL of dehydrated DMF and stirred at 70° C. for 12 hours. The reaction solution was added dropwise to 250 mL of deionized water. The resultant precipitate was collected by suction filtration, washed with deionized water, and then dried under reduced pressure to give a cyclodextrin polymer (white-yellow solid, 1.23 g). The IR spectrum of the resultant polymer showed an absorption peak for the carbonyl (C=O) stretching vibration of the carbamoyl group (NH—C(=O)—). Water solubility of the polymer was at most 1 wt % at 25° C.

Using the resultant cyclodextrin polymer, PFHxA was adsorbed and then subjected to a recovery experiment under the same conditions as those for the β-CD-supported polystyrene particles. Table 2 below shows the results.

TABLE 2

| Cleaning solvent | Adsorbent amount | Amount of adsorbed PFHxA | Stirring time | Amount of recovered PFHxA (recovery rate) |
|---|---|---|---|---|
| Acetone (1 mL) | 100 mg | 1.0 mg | 3 h | 0.40 mg (40%) |
|  |  |  | 15 h | 0.42 mg (42%) |
|  |  |  | 24 h | 0.49 mg (49%) |

The PFHxA recovery rate was up to 49%. The recovery rate (88% to 100%) obtained with the β-CD-supported polystyrene particles (PS-N-β-CD) according to the present invention is significantly higher than this recovery rate.

Highly Porous Chloromethylated Polystyrene Particles

Highly porous chloromethylated polystyrene particles (manufactured by Mitsubishi Chemical Corporation) were used (particle size 50-300 μm, pore radius 260 Å, pore volume 0.60 ml/g, specific surface area 41 m$^2$/g, 5.6 mmol/Cl/1 g).

Synthesis of β-CD-supported Polystyrene Particles (HP-PS-N-β-CD) with Highly Porous Chloromethylated Polystyrene Particles

[Chemical Formula 14]

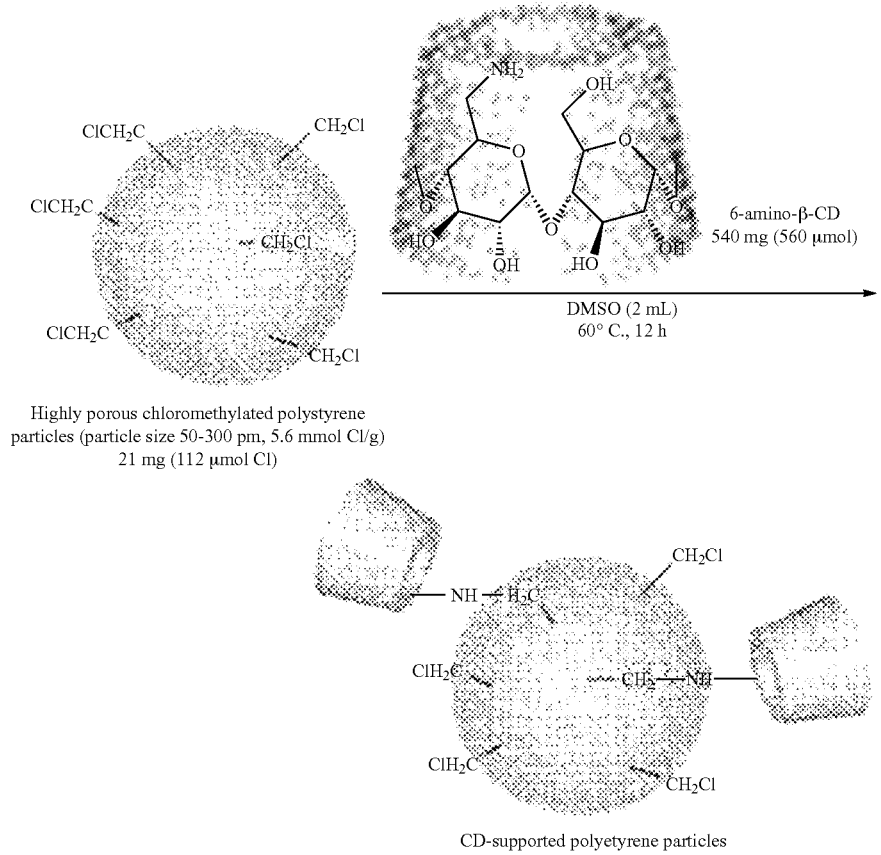

CD-supported polyetyrene particles

To 2 mL of a dimethylsulfoxide (DMSO) solution containing 0.64 g (560 μmol) of the obtained 6-amino-β-CD was added 0.021 g (112 μmol Cl) of the highly porous chloromethylated polystyrene particles (HP-PS-CH$_2$Cl particles) and stirred at 60° C. for 12 hours.

The polystyrene particle-containing DMSO solution was then subjected to filtration to give 0.023 g of CD-supported polystyrene particles (HP-PS-N-β-CD particles) were obtained.

Figure 11:
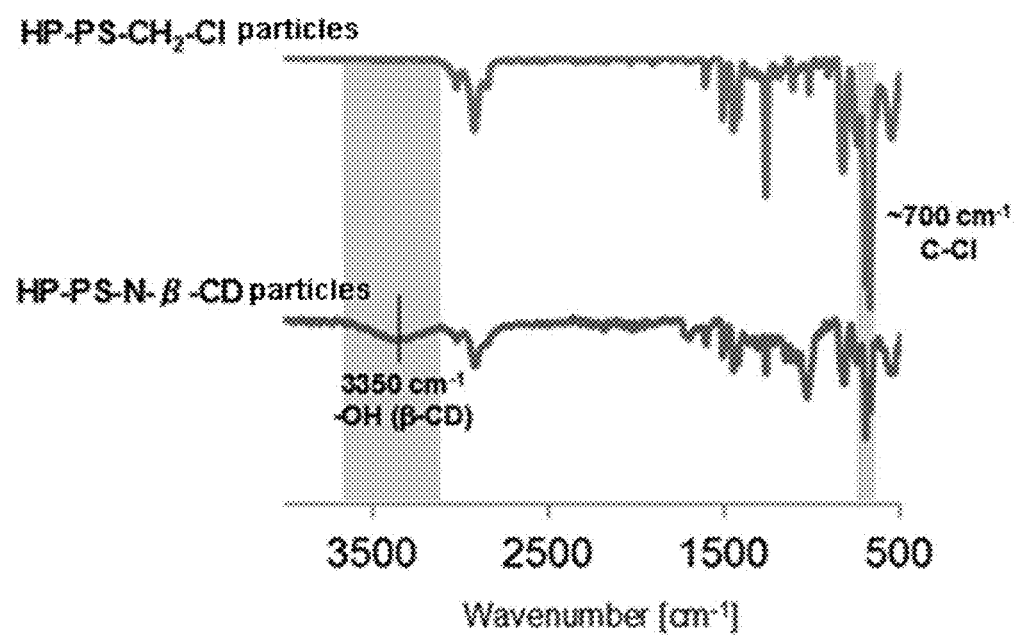
FIG. 11 is a chart of the FT-IR spectrum of HP-PS-N-β-CD particles.

FIG. 11 shows the FT-IR spectrum of the resultant particles together with that of the highly porous chloromethylated polystyrene particles. The intensity of the absorption for the C—Cl stretching vibration (about 700 cm$^{-1}$) of the chloromethyl group is lower in the spectrum of the HP-PS-N-β-CD particles than in that of the chloromethylated polystyrene particles. On the other hand, new absorption for the O—H stretching vibration of the CD hydroxyl group is observed at 3,350 cm$^{-1}$. It is, therefore, understood that 6-amino-β-CD is immobilized on the chloromethylated polystyrene particles.

The rate of modification with β-CD to Cl was about 3%. The resultant particles are named "HP-PS-N-β-CD (3%)."

The rate of modification with β-CD to Cl was calculated from the weight increase obtained by subtracting the weight of the chloromethylated polystyrene particles before the reaction from the weight of the CD-supported polystyrene particles obtained after the reaction.

Evaluation of Ability of β-CD-supported Polystyrene Particles (PS-NN-β-CD) to Adsorb Organic Fluoro-Compound (PFHxA) (1,000 ppm)

[Chemical Formula 15]

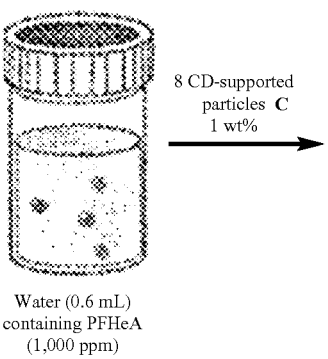

Water (0.6 mL) containing PFHeA (1,000 ppm)

8 CD-supported particles C 1 wt%

-continued

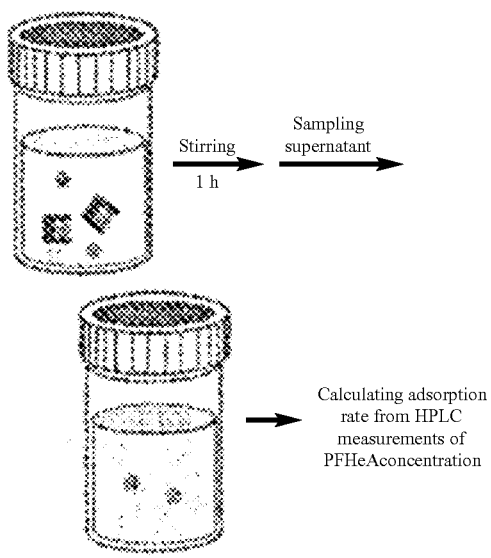

Stirring 1 h → Sampling supernatant

→ Calculating adsorption rate from HPLC measurements of PFHeA concentration

The obtained β-CD-supported polystyrene particles (HP-PS-N-β-CD) were added at 1% by weight based on the weight of water to 1 mL of an aqueous solution (pH 2.5) containing 1,000 ppm of perfluorohexanoic acid (PFHxA), and stirred with a magnetic stirrer at room temperature for 1 hour.

Subsequently, the supernatant was sampled and subjected to high-performance liquid chromatography (HPCL). The concentration of the remaining organic fluoro-compound in the supernatant was measured, and the rate of adsorption of the organic fluoro-compound removed by the adsorption was calculated to be 65% from the measured concentration.

The invention claimed is:

1. An adsorbent for an organic fluoro-compound, wherein cyclodextrin is supported on the surface of a water-insoluble polymer,
wherein the water-insoluble polymer comprises polystyrene particles,
wherein the polystyrene particles and the cyclodextrin are chemically bonded via a divalent linking group —X— in which
X is N, O, S, O(CH$_2$)$_n$O, with n being 1 to 6, or
X is O(CH$_2$CH$_2$O)$_n$, with n being 2 to 6, and
the hyphen "-" is a single bond; and
wherein the organic fluoro-compound is selected from the group consisting of fluoroalkane carboxylic acids (R—COOH), fluoroalkane sulfonic acids (R—SO$_3$H), fluoroalkyl alcohols (R—(CH$_2$)$_n$OH, with n being 1 to 6, and a mixture thereof, in which R is selected from the group consisting of CF$_3$(CF$_2$)$_n$, with n 0 to 11; HCF$_2$(CF$_2$)$_n$ with n being 0 to 11; CF$_3$(CF$_2$)$_n$O[CF(CF$_3$)CF$_2$O]$_m$CF(CF$_3$), with n being 0 to 5 and m being 0 to 5; and (CF$_3$)$_2$CF(CF$_2$)$_n$, with n being 0 to 10.

2. The adsorbent of claim 1, wherein X is N.

3. The adsorbent of claim 2, wherein synthesis is carried out by reacting cyclodextrin having an amino group substituted for at least one hydroxyl groups is reacted with the polystyrene particles having a chloromethyl group.

4. The adsorbent of claim 1, wherein the cyclodextrin is β-cyclodextrin.

5. A method for removal of an organic fluoro-compound, which comprises:
adsorbing the organic fluoro-compound with an adsorbent from an aqueous solution containing the organic fluoro-compound, wherein the adsorbent comprises cyclodextrin supported on the surface of a water-insoluble polymer,
wherein the water-insoluble polymer comprises polystyrene particles,
wherein the polystyrene particles and the cyclodextrin are chemically bonded via a divalent linking group —X— in which
X is N, O, S, O(CH$_2$)$_n$O, with n being 1 to 6, or
X is O(CH$_2$CH$_2$O)$_n$, with n being 2 to 6, and
the hyphen "-" is a single bond; and
wherein the organic fluoro-compound is selected from the group consisting of fluoroalkane carboxylic acids (R—COOH), fluoroalkane sulfonic acids (R—SO$_3$H), fluoroalkyl alcohols (R—(CH$_2$)$_n$OH, with n being 1 to 6, and a mixture thereof, in which R is selected from the group consisting of CF$_3$(CF$_2$)$_n$, with n being 0 to 11; HCF$_2$(CF$_2$)$_n$ with n being 0 to 11; CF$_3$(CF$_2$)$_n$O[CF(CF$_3$)CF$_2$O]$_m$CF(CF$_3$), with n being 0 to 5 and m being 0 to 5; and (CF$_3$)$_2$CF(CF$_2$)$_n$, with n being 0 to 10.

6. A method for recovery of an organic fluoro-compound, which comprises:
adsorbing the organic fluoro-compound with an adsorbent from an aqueous solution containing the organic fluoro-compound; and
washing the adsorbed organic fluoro-compound with an organic solvent,
wherein the adsorbent comprises cyclodextrin supported on the surface of a water-insoluble polymer,
wherein the water-insoluble polymer comprises polystyrene particles,
wherein the polystyrene particles and the cyclodextrin are chemically bonded via a divalent linking group —X— in which
X is N, O, S, O(CH$_2$)$_n$O, with n being 1 to 6, or
X is O(CH$_2$CH$_2$O)$_n$, with n being 2 to 6, and
the hyphen "-" is a single bond; and
wherein the organic fluoro-compound is selected from the group consisting of fluoroalkane carboxylic acids (R—COOH), fluoroalkane sulfonic acids (R—SO$_3$H), fluoroalkyl alcohols (R—(CH$_2$)$_n$OH, with n being 1 to 6, and a mixture thereof, in which R is selected from the group consisting of CF$_3$(CF$_2$)$_n$, with n being 0 to 11; HCF$_2$(CF$_2$)$_n$ with n being 0 to 11; CF$_3$(CF$_2$)$_n$O[CF(CF$_3$)CF$_2$O]$_m$CF(CF$_3$), with n being 0 to 5 and m being 0 to 5; and (CF$_3$)$_2$CF(CF$_2$)$_n$, with n being 0 to 10.

* * * * *